United States Patent [19]

Pierdet et al.

[11] 4,105,761

[45] Aug. 8, 1978

[54] ANABOLISANT-ANDROGENIC COMPOUNDS

[75] Inventors: André Pierdet, Noisy-le-Sec; Geneviéve Azadian, Paris, both of France

[73] Assignee: Roussel Uclaf, Paris, France

[21] Appl. No.: 553,249

[22] Filed: Feb. 26, 1975

[30] Foreign Application Priority Data

Sep. 20, 1974 [FR] France .............................. 74 31840

[51] Int. Cl.$^2$ ............................................. A61K 31/56
[52] U.S. Cl. ........................... 424/243; 260/239.55 C; 260/397.45; 260/397.5
[58] Field of Search .......................................... 424/243

[56] References Cited

U.S. PATENT DOCUMENTS

| 3,576,828 | 4/1971 | Anner et al. ....................... 260/397.3 |
|---|---|---|
| 3,629,244 | 12/1971 | Costerousse et al. ............ 424/243 X |
| 3,708,474 | 1/1973 | Nedelec et al. ................... 424/243 X |

OTHER PUBLICATIONS

Chem. Abstracts 70:58125f.

*Primary Examiner*—Ethel G. Love
*Attorney, Agent, or Firm*—Hammond & Littell

[57] ABSTRACT

Anabolisant-androgenic compositions comprising an effective amount of 17$\beta$-n-amyloxy-$\Delta^{4,9,11}$-estratriene-3-one and a pharmaceutical carrier and to a novel method of inducing androgenic and anabolisant activity in humans and other warm-blooded animals by administration of an effective amount of 17$\beta$-n-amyloxy-$\Delta^{4,9,11}$-estratriene-3-one.

2 Claims, No Drawings

ANABOLISANT-ANDROGENIC COMPOUNDS

STATE OF THE ART

Various $\Delta^{4,9,11}$-trienic steroids containing an ether group in the 17-position are known and French Pat. No. 1,492,985 describes a certain number of them. It is also known that some of there steroids have androgenic and anabolisant activity. Commonly assigned application Ser. No. 541,387 filed Jan. 16, 1975 describes 17$\beta$-n-amyloxy-$\Delta^{4,9,11}$-estratriene-3-one in animal feeds to promote the growth of animals.

OBJECTS OF THE INVENTION

It is an object of the invention to provide novel androgenic and anabolisant compositions without any significant hepatotoxicity.

It is a further object of the invention to provide a novel method of inducing androgenic and anabolisant activity in humans and other warm-blooded animals.

These and other objects and advantages of the invention will become obvious from the following detailed description.

THE INVENTION

The novel androgenic and anabolisant compositions of the invention are comprised of an effective amount of 17$\beta$-n-amyloxy-$\Delta^{4,9,11}$-estratriene-3-one and a pharmaceutical carrier. The compositions may be in the form of tablets, cachets, capsules or injectable solutions or suspensions prepared in the usual fashion.

The compositions have a very superior androgenic and anabolisant activity as compared to other closely related steroids and have a very weak hepatotoxicity. They are useful for combatting asthenia, thinness, osteoporosis and impotency.

The novel method of the invention for inducing androgenic and anabolisant activity in humans and other warm-blooded animals comprises administering to humans and other warm-blooded animals an effective amount of 17$\beta$-n-amyloxy-$\Delta^{4,9,11}$-estratriene-3-one. The said product may be administered transcutaneously or preferably orally. The usual daily dosage is 0,02 to 2 mg/Kg when administered orally.

17$\beta$-n-amyloxy-$\Delta^{4,9,11}$-estratriene 3-one may be prepared by reacting a compound of the formula

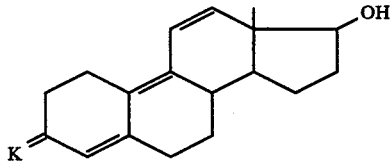

wherein K is a ketal with an alkaline agent and then with a pentyl halide to form a compound of the formula

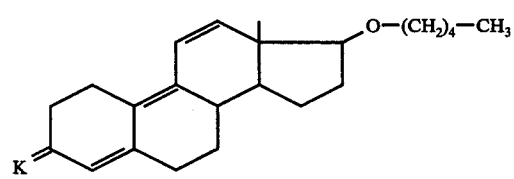

and reacting the latter with an acid hydrolysis agent to obtain 17$\beta$-n-amyloxy-$\Delta^{4,9,11}$-estratriene-3-one.

K is preferably a cyclic alkyl ketal group of 2 to 4 carbon atoms such as ethyleneketal or propyleneketal or a dialkylketal such as dimethylketal or diethylketal. The alkaline agent is preferably a strong base such as alkali metal amides, alkali metal hydrides such as sodium hydride, or alkali metal, or alkali metal alcoholate or an alkali metal organometallic compound. The reaction of the compound of formula I with the alkaline agent is preferably effected in an organic solvent such as tetrahydrofuran.

The pentyl halide is preferably the bromide, iodide or chloride and the acid hydrolysis agent is preferably hydrochloric acid, sulfuric acid, acetic acid, citric acid or p-toluene sulfonic acid.

In the following examples there are described several preferred embodiments to illustrate the invention. However, it should be understood that the invention is not intended to be limited to the specific embodiments.

EXAMPLE 1

17 $\beta$-n-amyloxy-$\Delta^{4,9,11}$-estratriene-3-one

STEP A:

3-ethylenedioxy-17$\beta$-n-amyloxy-$\Delta^{4,9,11}$-estratriene 22.5 ml of dimethylsulfoxide were added to a suspension of 4.5 g of 50% oily suspension of sodium hydride in 90 ml of tetrahydrofuran and the resulting suspension was stirred for 30 minutes at 22° C. 3 g of 3-ethylenedioxy-$\Delta^{4,9,11}$-estratriene-17$\beta$-ol was added all at once. The suspension was then stirred at 22° C for 17 hours and then $\alpha$ml of water were added dropwise thereto. The mixture was extracted with methylene chloride and the extracts were washed with water, dried and evaporated to dryness to obtain 4.3 g of 3-ethylenedioxy -17$\beta$-n-amyloxy-$\Delta^{4,9,11}$-estratriene in the form of a resin used as is for the next step.

STEP B: 17$\beta$-n-amyloxy-$\Delta^{4,9,11}$-estratriene-3-one 4.3 g of the resin of Step A were added to a solution of 80 ml of tetrahydrofuran and 40 ml of 50% acetic acid in water and the solution was stirred for 1 hour. The solution was poured into water and the mixture was neutralized with sodium bicarbonate and was extracted with methylene chloride. The organic extracts were washed with water, dried and distilled to dryness to obtain 6.5 g of an oil which was chromatographed over silica gel and was eluted with isopropyl ether to obtain 1.510 g of 17$\beta$-n-amyloxy-$\Delta^{4,9,11}$-estratriene-3-one.

EXAMPLE 2

A tablet composition was prepared by through admixture of 25 mg of 17$\beta$-n-amyloxy-$\Delta^{4,9,11}$-estratriene 3-one and sufficient excipient of talc, starch and magnesium stearate and compressing the mixture into tablets.

PHARMACOLOGICAL DATA

A. Anabolisant-androgenic activity

This test was effected using the technique of Hershberger [Proc. Soc. Exp. Biol. Med., Vol. 83 (1953), p. 175] slightly modified and groups of 5 male rats 19 to 21 days old were castrated and then were treated daily for 10 days by oral administration of the test product in a solution containing 0.5 ml of olive oil and 0.5 ml of water containing 0.25% of carboxymethylcellulose.

The animals were killed 24 hours after the last treatment and the prostate and seminal vesicles were removed and fixed for 24 hours in a solution of 10% formol in physiological serum. They were then dissected and weighed and the levator ani was removed and weighed in a fresh state. The increase in the weight of the genital organs indicate the anabolisant-androgenic activity of 17β-n-amyloxy-$\Delta^{4,9,11}$-estratriene-3-one and the results are reported in Table I and compared to the results of other trienic steroids.

TABLE I

| Test Products | Daily Doses in μg/rat | Levator ani in mg | Seminal Vesicules in mg | Prostate in mg |
|---|---|---|---|---|
| 17β-n-amyloxy $\Delta^{4,9,11}$-estratriene-3-one | 0 | 18.7 | 5.5 | 11.2 |
| | 10 | 28.4 | 13.1 | 27.7 |
| | 30 | 47.1 | 23.5 | 44.7 |
| | 90 | 53.1 | 64.0 | 79.0 |
| 17β-n-propyloxy-$\Delta^{4,9,11}$-estratriene-3-one | 0 | 11.4 | 4.3 | 9.8 |
| | 100 | 25.3 | 14.9 | 33.5 |
| | 1000 | 38.7 | 66.8 | 74.4 |
| 17β-(2'-methyl)-allyloxy-$\Delta^{4,9,11}$-estratriene-3-one | 0 | 13.0 | 4.5 | 7.0 |
| | 20 | 29.0 | 17.0 | 34.1 |
| | 100 | 23.5 | 16.7 | 39.0 |
| | 500 | 37.5 | 52.3 | 66.2 |
| 17β-(cyclopropyl)-methoxy-$\Delta^{4,9,11}$-estratriene-3-one | 0 | 14.3 | 4.7 | 7.6 |
| | 10 | 20.7 | 9.9 | 18.4 |
| | 100 | 33.3 | 26.4 | 41.7 |
| | 1000 | 49.2 | 97.1 | 88.7 |
| 17β-isobutyloxy-$\Delta^{4,9,11}$-estratriene-3-one | 0 | 14.3 | 4.7 | 7.6 |
| | 10 | 24.6 | 9.2 | 13.5 |
| | 100 | 41.9 | 28.7 | 46.4 |
| | 1000 | 44.0 | 116.0 | 104.8 |
| 17β-(3'-methyl)but-2'-enyloxy-$\Delta^{4,9,11}$-estratriene-3-one | 0 | 24.1 | 4.8 | 8.4 |
| | 10 | 28.7 | 8.2 | 12.8 |
| | 100 | 49.2 | 36.7 | 39.0 |

The results of Table I show that the anabolisant-androgenic activity of 17β-n-amyloxy-$\Delta^{4,9,11}$-estratriene-3-one when administered orally is clearly much superior to other $\Delta^{4,9,11}$-estratrienes.

B. Hepatonocivity study

17β-n-amyloxy-$\Delta^{4,9,11}$-estratriene-3-one was orally administered for 4 consecutive days to a rabbit at a dose of 10 mg/kg and the animal was killed on the 5th day. This caused an increase in the rate of oxalacetic transaminase (SGOT) without having caused a change in the rate of retention of bromosulfonephtalein. (BSP). The product at 5 mg/kg was well tolerated by the hepatic cells.

Various modifications of the composition and process of the invention may be made without departing from the spirit or scope thereof and it is to be understood that the invention is to be limited only as defined in the appended claims.

We claim:

1. An androgenic and anabolisant composition comprising an effective amount to obtain androgenic and anabolic activity of 17β-n-amyloxy-$\Delta^{4,9,11}$-estratriene-3-one and an oral pharmaceutical carrier.

2. A method of inducing androgenic and anabolisant activity in humans and other warm-blooded animals comprising orally administering to humans and other warm-blooded animals an androgenic and anabolisant effective amount of 17β-n-amyloxy-$\Delta^{4,9,11}$-estratriene-3-one.

* * * * *